US012593868B2

(12) United States Patent
Alagia et al.

(10) Patent No.: US 12,593,868 B2
(45) Date of Patent: Apr. 7, 2026

(54) DISPENSER FOR DISCHARGING A NICOTINE- AND/OR CANNABIS-CONTAINING FLUID

(71) Applicant: Aptar Radolfzell GmbH, Radolfzell (DE)

(72) Inventors: Pierluigi Alagia, Moos (DE); Jürgen Greiner-Perth, Gottmadingen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 180 days.

(21) Appl. No.: 18/702,410

(22) PCT Filed: Oct. 4, 2022

(86) PCT No.: PCT/EP2022/077604
§ 371 (c)(1),
(2) Date: Apr. 18, 2024

(87) PCT Pub. No.: WO2023/066658
PCT Pub. Date: Apr. 27, 2023

(65) Prior Publication Data
US 2024/0415173 A1 Dec. 19, 2024

(30) Foreign Application Priority Data
Oct. 19, 2021 (EP) .................................... 21203534

(51) Int. Cl.
*A24F 40/10* (2020.01)
*A24F 40/42* (2020.01)
(Continued)

(52) U.S. Cl.
CPC .............. *A24F 40/10* (2020.01); *A24F 40/42* (2020.01); *A24F 40/485* (2020.01); *A61M 15/009* (2013.01)

(58) Field of Classification Search
CPC ........ A24F 40/10; A24F 40/42; A24F 40/485; A61M 15/009; A61M 15/0021
See application file for complete search history.

(56) References Cited

U.S. PATENT DOCUMENTS 3,434,633 A 3/1969 Green
10,632,487 B2 4/2020 Greiner-Perth et al.
(Continued)

FOREIGN PATENT DOCUMENTS

DE 202019005638 U1 5/2021
WO 2012159026 A1 11/2012
(Continued)

OTHER PUBLICATIONS

International Search Report, with English translation, issued in corresponding International Application No. PCT/EP2022/077604, date of mailing Jan. 9, 2023 (5 pages).
(Continued)

*Primary Examiner* — Jennifer C Chiang
(74) *Attorney, Agent, or Firm* — FLYNN THIEL, P.C

(57) ABSTRACT
A fluid dispenser for discharging a nicotine and/or cannabis-containing fluid as a replacement for tobacco products consumed by burning same, including a fluid store for storing the fluid before output, a mouthpiece for discharging the fluid, a connecting fluid channel and an outlet valve assembly, with which the fluid channel is opened and closed. The outlet valve assembly has an elastically deformable tube section forming part of the fluid channel, and an actuation surface is located on an outer side of the dispenser for actuating the outlet valve assembly. This actuation surface is coupled to a tube-shaping segment, with which the tube section is deformed from a state in which the fluid channel is closed into a state in which the fluid channel is open by applying force to the actuation surface, to thereby allow for the discharge of fluid.

32 Claims, 10 Drawing Sheets

(51) Int. Cl.
    *A24F 40/485*      (2020.01)
    *A61M 15/00*      (2006.01)

(56)            References Cited

U.S. PATENT DOCUMENTS

| | | |
|---|---|---|
| 12,048,806 B2 * | 7/2024 | Moloney .............. A61M 11/042 |
| 2002/0008122 A1 | 1/2002 | Ritsche et al. |
| 2020/0277126 A1 | 9/2020 | Sell |
| 2023/0276862 A1 * | 9/2023 | Greiner-Perth ......... A24F 42/60 |
| | | 131/273 |

FOREIGN PATENT DOCUMENTS

| | | |
|---|---|---|
| WO | 2012159028 A1 | 11/2012 |
| WO | 2017191205 A1 | 11/2017 |
| WO | 2019224531 A1 | 11/2019 |

OTHER PUBLICATIONS

Written Opinion of International Searching Authority, issued in corresponding International Application No. PCT/EP2022/077604, date of mailing Jan. 9, 2023 (5 pages).

* cited by examiner

DISPENSER FOR DISCHARGING A NICOTINE- AND/OR CANNABIS-CONTAINING FLUID

FIELD OF APPLICATION AND PRIOR ART

The invention relates to liquid dispensers for discharging a liquid, in particular a nicotine-containing and/or cannabis-containing liquid.

Liquid dispensers of this type replace the consumption of tobacco products. Instead of tobacco or other solids being burned, nicotine-containing and/or cannabis-containing liquid in atomized form is consumed by the user. Liquid dispensers of the generic type are used regularly in daily life by their users. It is desirable that they can be actuated in an intuitive way.

Problem and Solution

It is primarily a problem of the invention to provide structural possibilities for realizing a dispenser of this type for discharging nicotine-containing and/or cannabis-containing liquids, in particular a dispenser with a reliable outlet valve which can be produced inexpensively.

In order to solve this problem, a liquid dispenser is proposed with a liquid store for storing the liquid before the discharge, and with a mouthpiece, through which the liquid can be output. A liquid channel extends between the liquid store and the mouthpiece, through which liquid channel liquid can pass to the mouthpiece. The liquid channel is provided with an outlet valve arrangement, by way of which the liquid channel can be closed and opened.

In particular, a liquid dispenser according to the invention can have an elongate and slim shape which extends in the direction of a main direction of extent, and can be handled in a similar manner to a cigarette. The mouthpiece and the liquid store which is preferably provided so as to lie opposite the former preferably extend in each case in the direction of this main direction of extent. An outer side of the liquid dispenser can have a uniform cylindrical shape. The liquid dispenser is preferably configured, however, with a greater cross section in the region of the liquid store than in the region of the mouthpiece.

The mouthpiece is enclosed by the lips of the user or is gripped in the teeth when liquid is to be discharged. The mouthpiece preferably has an approximately tubular design with an end-side outlet opening. The outlet opening preferably has an inside cross section of at least 20 mm$^2$. The liquid is fed in within the mouthpiece, which liquid is, in particular, preferably atomized in the process for the purpose of consumption. The mouthpiece is preferably connected via a further channel to the surrounding area, with the result that air can also be sucked in together with the liquid by the user. This air inlet channel is preferably provided as a radially oriented opening in a wall of the mouthpiece.

In the state in which it is ready for sale, the liquid store is filled with the discharging liquid, that is to say in particular with a nicotine-containing and/or cannabis-containing liquid. The volume of the liquid store preferably lies at less than 100 ml, in particular preferably at less than 30 ml.

In accordance with two aspects of the invention, different designs of the outlet valve arrangement are proposed which might also be realized together, however.

It is provided in accordance with a first aspect of the invention that the outlet valve arrangement has an elastically deformable hose portion which forms at least one part of the liquid channel.

In order for it to be possible for the outlet valve arrangement to be opened and closed, an actuating surface is provided on an outer side of the dispenser, in particular for manual actuation or for actuation using the mouth. This actuating surface can be moved with respect to a housing part which surrounds the liquid channel and/or with respect to the liquid store, and is coupled to a hose forming segment which converts a movement, brought about by way of the user, of the actuating surface into a deformation or return to the original shape of the hose portion. By way of the actuating surface being loaded with force, the hose portion can therefore be deformed out of a state which closes the liquid channel into a state which opens the liquid channel. A restoring spring is preferably provided, by way of which the actuating surface is loaded with force in the direction of its non-actuated end position, and counter to the force of which the actuation of the actuating surface takes place.

Two different concepts for using the hose portion as part of the outlet valve arrangement are preferred. The first of the concepts is based on a compression of the hose, and the second of the concepts is based on bending of the hose.

The valve which is formed by way of the hose portion and the hose forming segment which acts thereon preferably forms the last valve in the flow current before the discharge of the liquid through the mouthpiece. When the hose forming segment is in a position, in which the throughflow of the hose portion is not prevented by way of the hose forming segment, the liquid can therefore escape.

In the case of the first concept, the hose forming segment can be moved orthogonally with respect to the hose portion. In one possible design, it can be movable exclusively orthogonally, that is to say it can have a movement direction which is oriented at a 90° angle with respect to the direction of extent of the hose portion. The movability of the hose forming segment can also have an orthogonal component, but also at the same time can be movable parallel to the direction of extent of the hose portion.

The movement of the hose forming segment takes place between a closing end position and an opening end position. In the closing end position, the hose forming segment presses from outside against the hose section and therefore presses the latter against a counter-surface, in particular against a stationary holding surface, for example a holding surface on an inner circumference of a tube portion which partially encloses the hose portion. The inside cross section of the hose portion is tapered largely or even to zero as a result.

In the opening end position, the hose forming segment is moved away from the hose portion, with the result that the elastic hose portion can be relieved again under the effect of the liquid pressure, and permits the flow of liquid through the hose portion.

The actuating surface is preferably pressed in, in the direction of a center or a central axis, for the purpose of discharge. In order to bring about a movement of the hose forming segment away from the hose portion as a result, a movement direction reversal can be provided between the actuating surface and the hose forming segment, with the result that the hose forming segment is moved in a movement direction which differs from the movement direction of the actuating surface. This can be achieved simply, for example, via a tilting element which has the hose forming segment and the actuating surface on opposite sides of a tilting axis.

Another possible design provides that the hose forming segment and the actuating surface are provided on sides of the hose portion which lie opposite one another. The actuating surface and the hose forming segment are then moved approximately in an identical direction, preferably in an exactly identical direction and to an identical extent. In the case of a design of this type, the combination of actuating surface and hose forming segment engages around the hose portion.

In the case of the second concept, the closure of the outlet valve arrangement is based on bending of the hose. Here, the hose forming segment can be moved between a closing end position and an opening end position, preferably by way of fixed or even single-piece connection of the hose forming segment to the actuating surface.

In the closing end position, the hose forming segment forces the hose portion into a closed state, in which the hose portion is bent at least once in at least one bending region. Here, the hose portion is bent to such an extent that inner surfaces of the hose portion which lie opposite one another bear sealingly against one another in the bending region. The cross section, which is, for example, round in a relief state, of the hose changes its shape in the direction of the bending region as far as an initially elliptical shape which narrows in a linear manner at the actual bending point and, as a result, allows the cross section to decrease to zero. This bending point forms the cut-off point of the outlet valve. The hose portion preferably bends by at least 90°, in particular by at least 105°, at the bending point. The tightest curvature radius on an outer side of the hose portion at the bending point is preferably smaller than three times the diameter of the hose portion, in particular preferably smaller than two times the diameter of the hose portion.

As soon as the hose forming segment has returned into its opening end position, the curvature region returns into a more relieved state of the hose portion, in which the inside cross section of the hose portion opens again at the bending point. The hose portion can now be flowed through again by liquid. In the opened state, the hose portion directions on both sides of the bending point preferably differ from one another by less than 90°, in particular preferably by less than 75°.

Whether liquid can pass through a bent hose portion is also dependent on the liquid pressure. It can be advantageous if the hose portion has a plurality of bending regions, in particular two bending regions, at which the inside interior cross section of the hose portion at the bending point narrows in each case to zero or approximately zero. Two or more bending regions of this type which are narrowed at the same time when the actuating surface is pressed down can together achieve the valve action, by, although a first bending region remains capable of being flowed through by highly pressurized liquid, it lowering the pressure sufficiently such that the bending point in the second bending region can completely prevent the throughflow.

In the case of more than one bending point, it is particularly advantageous if the hose portion bends in the two bending regions in opposite directions, that is to say in the manner of a Z-shape. A Z-shape of this type allows it to be possible for the adjoining hose parts to have an identical direction of extent on the outer side of the bending regions and to be connected by way of a connecting segment which in each case forms a bending region with the hose parts on both sides. The adjoining hose parts are offset with respect to one another, however, in a case of this type.

In order to prevent this, it can be advantageous if the hose portion has a total of four bending regions which form the corners of a parallelogram shape and of which two are bent in a liquid-sealing manner in the case of arrangement of the hose forming segment in the closing end position, that is to say have an inside diameter of zero in the region of their respective bending point. The other two bending regions do not close when the hose forming segment is pressed into its closing end position, but rather reduce their bending angle.

Depending on the type of deformation of the hose portion which is required in order to open the outlet valve arrangement, the hose forming segment can be separate from this hose portion and can be pressed against the hose only in the case of the actuating surface being loaded with force. The hose forming segment can also, however, have a coupling portion for permanent coupling to the hose portion, for example in the form of a laterally slotted hose clamp, into which the hose portion is inserted. Coupling of this type is appropriate, in order for it to be possible for the hose portion to be moved reliably both during the transfer into the closed state and during the transfer into the open state, without it being necessary for this purpose for the inherent restoring tendency of the hose portion or the restoring tendency brought about by way of the liquid pressure to be utilized.

A liquid dispenser of the described type is used as required by the user, usually multiple times per day. The user moves the liquid dispenser for use to the correct position, that is to say in particular to the mouth, and then presses on the actuating surface.

This pressure can be, in the case of one refinement, a manually applied pressure. The user therefore presses, for example, with the index finger on the actuating surface on a button or a slider which is provided for this purpose. The actuating surface is moved with respect to the housing, and the outlet valve arrangement is opened as a result.

The actuating surface can preferably be pressed in, in order to open the outlet valve arrangement, radially in relation to the main direction of extent of the liquid dispenser or a cylindrical part portion thereof. This design is suitable, in particular, for a highly simple construction with a hose forming segment which compresses the hose portion in a closing manner and is spaced apart from the hose portion by way of the actuating surface being loaded with force. Another preferred design provides that the actuating surface which is preferably provided for this purpose on a sleeve-shaped component can be moved axially in order to open the outlet valve arrangement.

In addition to the manual actuation, the actuation by the mouth is considered to be expedient. Here, the user exerts a pressure on the mouthpiece using their lips or their teeth, loading of the actuating surface with force also occurring.

For this purpose, the actuating surface is preferably arranged in the region of the mouthpiece and can be pressed down by way of the lips or teeth of the user. Here, the required force should as far as possible lie below 5 newtons.

The actuating surface can be pressed down with respect to the mouthpiece, in particular with respect to an opposite wall of the mouthpiece. In particular, the actuating surface can be of pivotably movable configuration here.

The actuating surface can also, however, be in one piece with the entire mouthpiece or be formed by way of the entire mouthpiece. This mouthpiece can then be moved, in particular can be moved axially, in its entirety in relation to a main direction of extent with respect to the liquid store or other housing portions of the liquid dispenser.

A liquid dispenser of the described type is preferably provided with a pressurized store, with the result that the liquid flows out automatically in the case of an open outlet valve arrangement.

In particular, the liquid store can be partially replaceable. To this end, it is proposed, in particular, that the liquid store has a receptacle for receiving a replaceable liquid cartridge.

A liquid cartridge is preferably inserted without tools into this receptacle. If an inserted cartridge is empty, the user can separate it from the receptacle and replace it with a new one.

Liquid cartridges of the described type preferably have an additional valve, by way of which the storage space thereof is separated from a surrounding area until use. This additional valve can be opened, in particular, by way of insertion of the liquid cartridge into the receptacle. In particular, the liquid cartridges have an outlet nozzle which is pressed in or tilted with respect to a store wall of the liquid cartridge during insertion into the receptacle and, as a result, opens the additional valve.

The liquid dispenser in accordance with the second aspect of the invention likewise has a liquid store for storing the liquid before discharge, a mouthpiece, by way of which the liquid can be output, and a connecting liquid channel which can be closed and opened by means of an outlet valve arrangement. All the features which are mentioned above in this regard can also be realized individually or in combination in the case of the liquid dispenser in accordance with this second aspect of the invention.

In the case of this second aspect of the invention, the outlet valve arrangement has a tilt valve which has a tiltably movable outlet nozzle which is penetrated by the liquid channel. The tilt valve is opened and closed in a manner which is dependent on the tilting position of the outlet nozzle. A tilt valve can be implemented technically, in particular, in such a way that a preferably circumferential valve surface is connected to the outlet nozzle, which valve surface is raised as a result of the tilting movement by a likewise preferably circumferential counter-surface and thus permits a liquid flow to the mouthpiece. The outlet nozzle can preferably be tilted in any desired direction, in order to be opened.

In addition to the described hose valve, a tilt valve has proven to be a particularly advantageous and inexpensive design of an outlet valve arrangement. It can be opened even by a small tilt, and nevertheless permits highly metered opening and closing.

The actuation of a tilt valve of this type can take place directly via the mouthpiece in the simplest case. For this purpose, the mouthpiece is of movable configuration with respect to the liquid store, and is coupled here to the outlet nozzle in such a way that a movement of the mouthpiece with respect to the liquid store tilts the outlet nozzle. This can be achieved, for example, by virtue of the fact that the mouthpiece is connected fixedly to the outlet nozzle, and the user opens the tilt valve by way of slight angling of the mouthpiece with respect to the liquid dispenser, preferably by an angle of less than 10°, and in this way makes the discharge of liquid possible.

It is also possible in the case of this liquid dispenser in accordance with the second aspect of the invention, however, for an actuating surface to be provided separately from the mouthpiece on the outer side of the dispenser, which actuating surface can be moved with respect to the liquid store and/or the mouthpiece, and which actuating surface is operatively coupled to the outlet nozzle, with the result that the outlet nozzle is tilted by way of the actuating surface being loaded with force. The manual actuation or an actuation using the mouth is also possible here, the actuating surface being positioned closer to the mouthpiece or further away therefrom depending on the desired type.

In the simplest case, the actuating surface can be movable orthogonally with respect to the outlet nozzle and, in the pressed-in state, can press the outlet nozzle into a tilted position.

If a movement of the outlet nozzle with respect to the mouthpiece is provided in the case of opening of the tilt valve, it can be expedient for a hose portion which can compensate for the offset which arises to be provided between the outlet nozzle and the mouthpiece.

The tilt valve can fundamentally be provided separately from a replaceable liquid cartridge. It is preferred, however, that the liquid store has a replaceable liquid cartridge, on which the tilt valve is provided directly. A replacement of the tilt valve therefore also takes place during the replacement of the liquid cartridge.

The liquid dispenser is preferably configured for outputting the liquid in a finely atomized form. This can be achieved, for example, via an atomizing device with a swirl chamber at the end of the liquid channel. One design is preferred, however, in the case of which a discharge nozzle unit is provided, through which liquid can be output into the mouthpiece. This discharge nozzle unit preferably has a plurality of nozzle openings, in particular a nozzle plate, in which a plurality of nozzle openings are provided. Here, the nozzle openings can be oriented in a diverging manner, in particular. A nozzle plate of this type makes the production of a particularly fine droplet jet possible, even in the case of an overall extremely low volumetric flow, as is desired in the case of the preferred fields of application of the liquid dispenser. The nozzle plate preferably has at least 10 nozzle openings. The inside cross section of the nozzle openings at the narrowest point is preferably less than 250 μm².

The abovementioned hose portion in the case of the first variant of the invention is preferably manufactured from an elastic plastic material, in particular from polyethylene, from polypropylene or from a material which contains polyethylene and/or polypropylene. Since, in the case of the preferred field of application of the discharge of nicotine-containing and/or cannabis-containing liquids, only small liquid flows are required, the hose portion preferably has an internal diameter of 2.0 mm or less, in particular of 1.0 mm or less. Furthermore, the hose portion preferably has a wall thickness of 1.0 mm or less, in particular preferably of 0.5 mm or less. The wall thickness is preferably 0.1 mm or more, in particular 0.3 mm or more. The internal diameter is preferably between 30% and 70% of the external diameter of the hose portion.

Although the above-described liquid dispensers are provided, in particular, for the abovementioned field of application of the discharge of nicotine-containing and/or cannabis-containing liquids, some aspects of the invention can also be realized separately from this.

A separate aspect of the invention is provided by one design of a liquid dispenser which has a liquid store, configured as a pressurized store, for storing the liquid before the discharge, and a discharge opening, it not absolutely being necessary for the discharge opening to be arranged in the region of a mouthpiece. The liquid store and the discharge opening are connected to one another via a liquid channel which is assigned an outlet valve arrangement, by means of which the liquid channel can be closed and opened. As explained above with respect to the second concept of the first variant of the invention, the outlet valve arrangement has an elastically deformable hose portion which forms a part of the liquid channel and at least one part of the outlet valve arrangement which can preferably be switched by the user by means of a handle.

In an open state of the outlet valve arrangement, the hose portion can be flowed through by liquid. In a closed state, the hose portion is bent at least once in at least one bending region, a plurality of bending points preferably being provided in the way which has already been described above. Inner surfaces of the hose portion which lie opposite one another bear sealingly against one another at the bending points, with the result that the hose portion cannot be flowed through by liquid.

This fundamental principle of the hose portion which is bent once or multiple times for forming a switchable outlet valve can be used in different liquid dispensers. In particular, this technology can be used in the case of the above-described nicotine or cannabis dispensers, but also for the discharge of a liquid medication, a mouth spray or a dental hygiene product. The liquid store which is preferably configured as a pressurized store receives a corresponding liquid in the case of designs of this type.

The above-described further possible features of a nicotine or cannabis dispenser can also be used individually or in combination in the case of a dispenser of this type in another field of application.

BRIEF DESCRIPTION OF THE DRAWINGS

Further advantages and aspects of the invention result from the claims and from the following description of preferred exemplary embodiments of the invention which are explained in the following text using the figures.

DETAILED DESCRIPTION OF THE
EXEMPLARY EMBODIMENTS

Figure 1A:
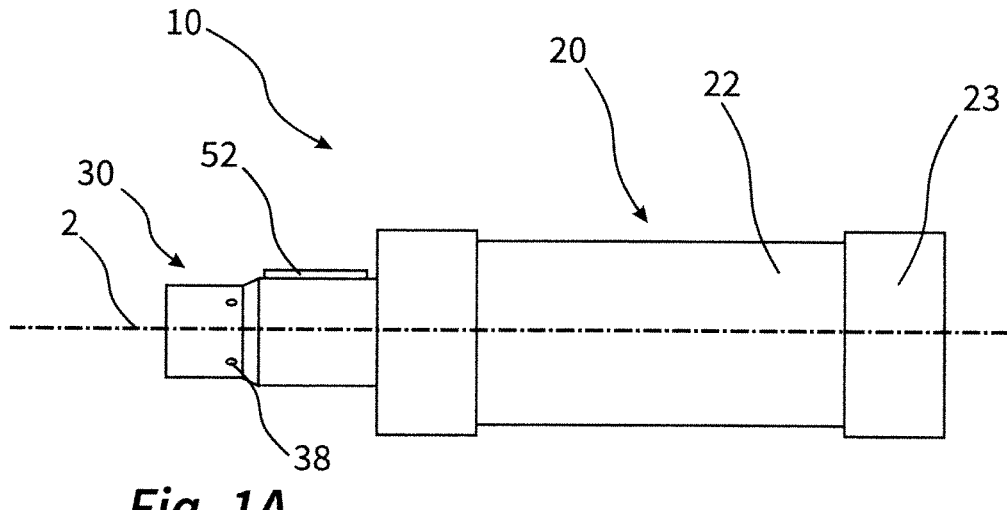
FIGS. 1A and 1B show a possible basic construction in generalized form of a liquid dispenser according to the invention.
Figure 1B:
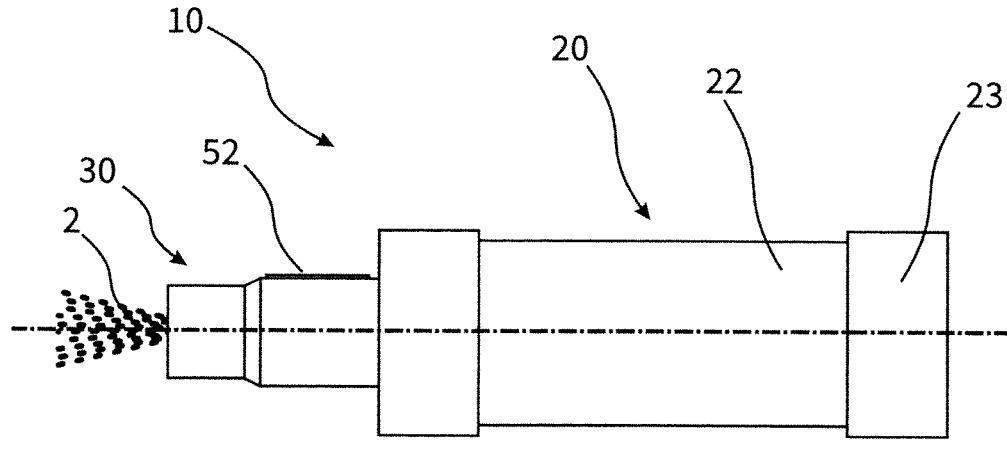

FIGS. 1*a* and 1B first of all show a preferred design of a liquid dispenser according to the invention in a non-sectioned illustration. A liquid dispenser 10 of this type which is provided, in particular, for the discharge of nicotine-containing or cannabis-containing liquid has a shape which is oriented in the direction of a main direction of extent 2. A mouthpiece 30 is provided at a proximal end of the liquid dispenser 10. A liquid store 20 is provided at an opposite distal end, which liquid store 20 has, in the case of the example of FIGS. 1A and 1B, a shaft-shaped receptacle 22 which is closed by a lock 23 and serves to receive a pressurized store cartridge which cannot be seen in FIGS. 1A and 1B. A connecting liquid channel 40 (not shown in FIGS. 1A and 1B) which has an outlet valve arrangement 50 is provided between the liquid store 20 and the mouthpiece 30. This outlet valve arrangement 50 allows the liquid channel 40 to open, starting from a state which is closed in the rest state, for example by means of an actuating surface 52. If the outlet valve arrangement 50 is open, liquid can flow through the liquid channel 40 to the mouthpiece 30 and can be discharged there in the form of an atomized spray jet, as illustrated in FIG. 1B. The liquid which is sprayed or atomized in this way is sucked in by the user, air preferably additionally also being sucked in through air inlet channels 38.

Figure 2A:
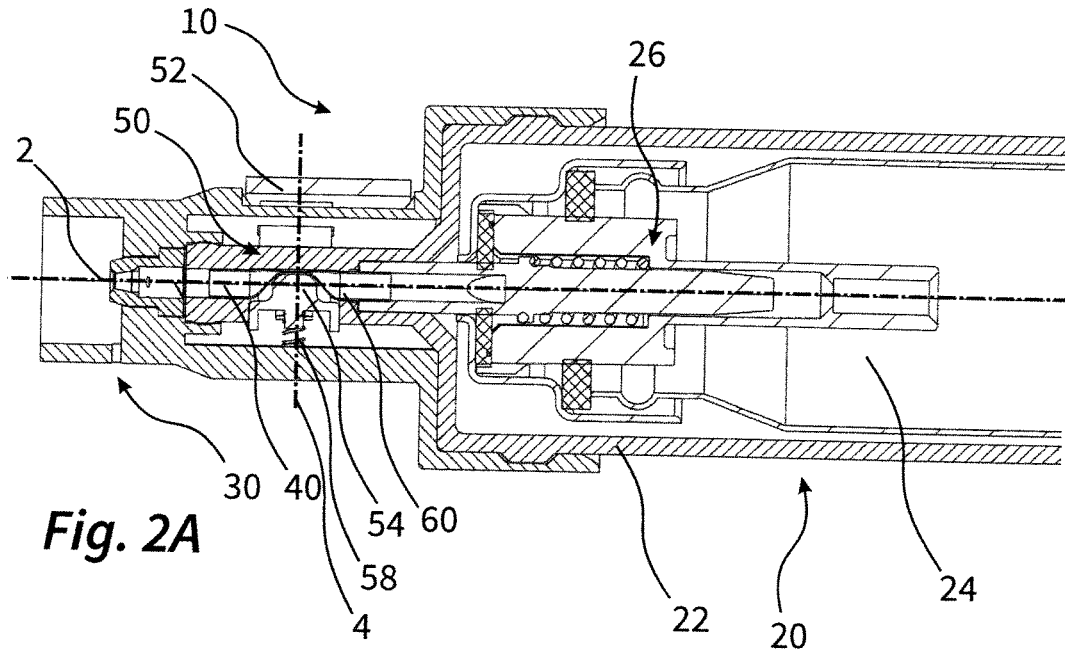
FIGS. 2A and 2B show the detailed construction of a first exemplary embodiment of a liquid dispenser according to the invention in the non-actuated state and in the actuated state.
Figure 2B:
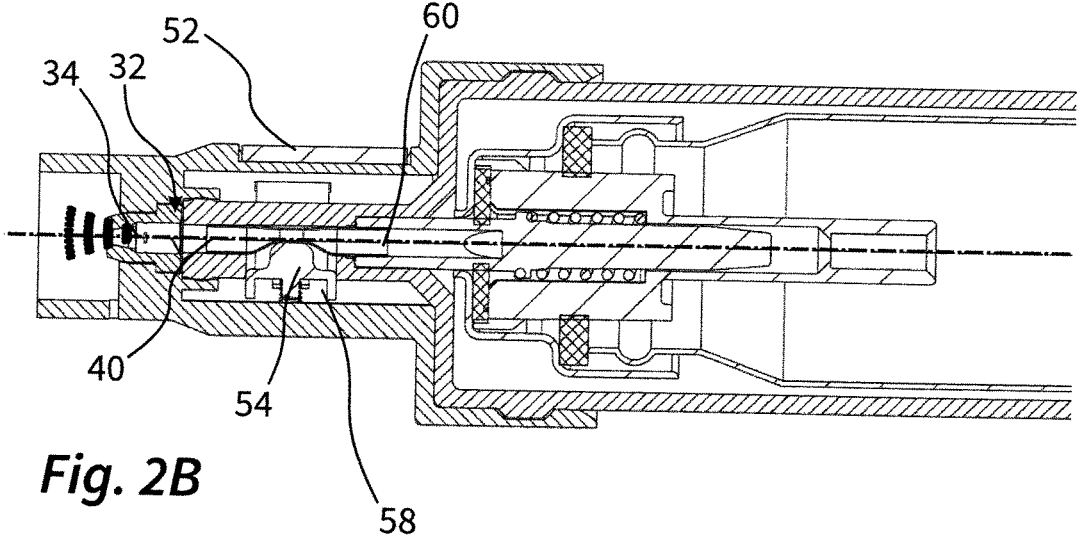

FIGS. 2A and 2B show a first exemplary embodiment in a sectioned illustration. It can be seen here that the above-mentioned liquid cartridge 24 which has an outlet valve 26 is arranged in the receptacle 22 of the liquid store 20. When the liquid cartridge 24 is received in the liquid dispenser 10, this outlet valve 26 is open.

A tubular housing portion extends from an outlet nozzle 27 of the liquid cartridge 24, within which tubular housing portion a hose portion 60 is positioned. The tubular housing portion which surrounds the hose portion 60 is provided with an opening on its lower side. A hose forming segment 54 which can be moved in the movement direction 4 and is pressed by means of a restoring spring 28 upward and therefore against the hose portion 60 is situated here.

In a rest state of the dispenser, the hose portion 60 is compressed hereby to such an extent that no liquid can flow in the direction of the mouthpiece 30 and to the discharge nozzle unit 32 which is arranged there. The abovementioned hose forming segment 54 is connected, for example, by means of a latching connection to an actuating component, at which the abovementioned actuating surface 52 is also provided. A single-piece design is also possible.

If the actuating surface 52 is then pressed down manually counter to the force of the restoring spring 58 in the way which is illustrated in FIG. 2B, a part of the force which acts on the hose portion 60 is therefore canceled, with the result that the liquid channel 40 is opened and liquid can flow to the discharge nozzle unit 32. Here, the liquid is pressed against a nozzle plate 34 which is provided with fine apertures and brings about the desired atomization of the liquid. During the actuation of the actuating surface 52, the user sucks on the mouthpiece 30 which is enclosed by their lips, air which can flow into the mouthpiece through an air inlet channel 38 also being sucked in, in addition to the liquid which is discharged through the discharge nozzle unit 32.

Figure 3A:
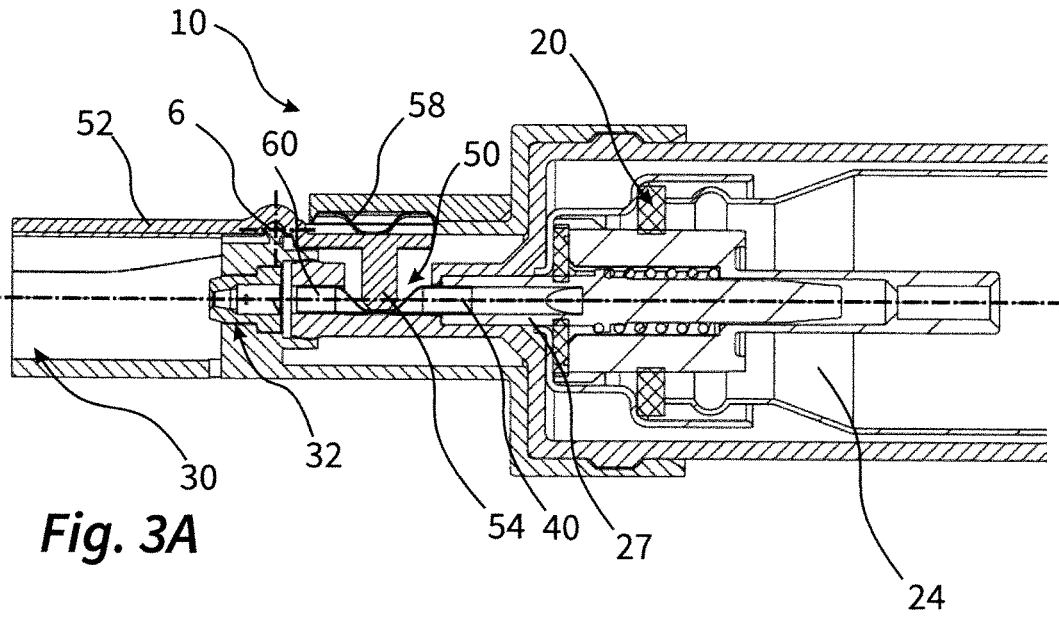
FIGS. 3A and 3B show the detailed construction of a second exemplary embodiment of a liquid dispenser according to the invention in the non-actuated state and in the actuated state.
Figure 3B:
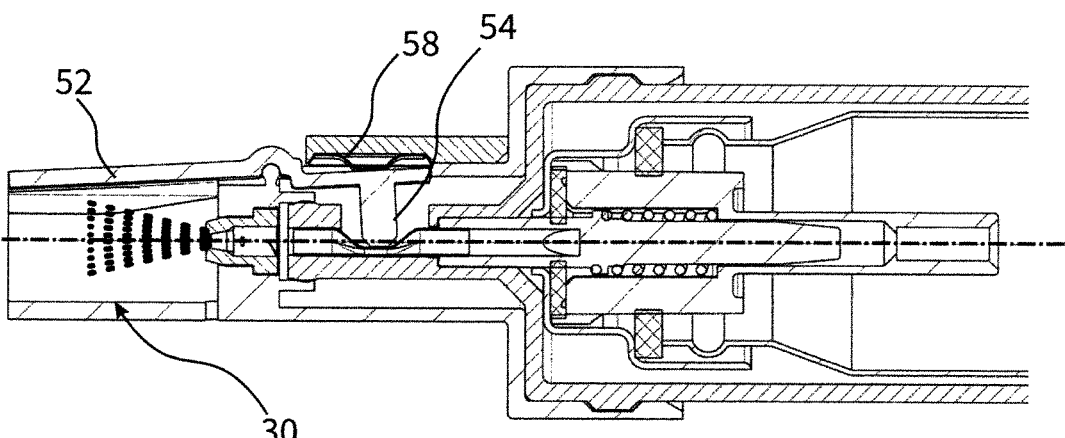

In the case of the exemplary embodiment of FIGS. 3A and 3B, the fundamental method of operation is highly similar. Here too, a liquid channel 40 which is formed in sections by way of a hose portion 60 is provided between an outlet nozzle 27 of a liquid cartridge 24 and the discharge nozzle unit 32. Here too, the hose portion 60 is compressed by way of a hose forming segment 54, the latter pressing from above onto the hose portion 60 in a difference from the design of FIGS. 2A and 2B. In the case of this design, the hose forming segment 54 is, together with the actuating surface 52, part of a common rocker element which can be pivoted about the pivot axis 6.

In the case of the exemplary embodiment of FIGS. 3A and 3B, opening of the outlet valve arrangement 50 takes place by way of the mouth. The actuating surface 52 therefore extends as far as into the region of the mouthpiece 30, and can be enclosed together with the mouthpiece 30 by the lips or the teeth or a user. If the user presses their lips or teeth together, the rocker element pivots counter to the clockwise direction in relation to the figures and therefore presses the hose forming segment 54 upward counter to the force of the restoring spring 58. As a result, the force which compresses the hose portion 60 is canceled, and the discharge of liquid occurs, as is illustrated in FIG. 3B.

Figure 4A:
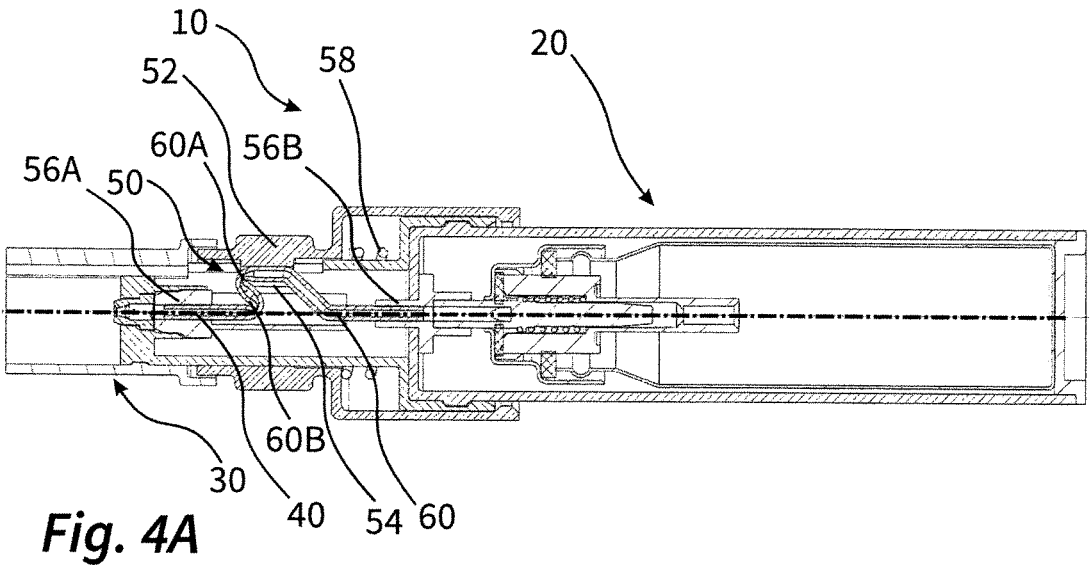
FIGS. 4A and 4B show the detailed construction of a third exemplary embodiment of a liquid dispenser according to the invention in the non-actuated state and in the actuated state.
Figure 4B:
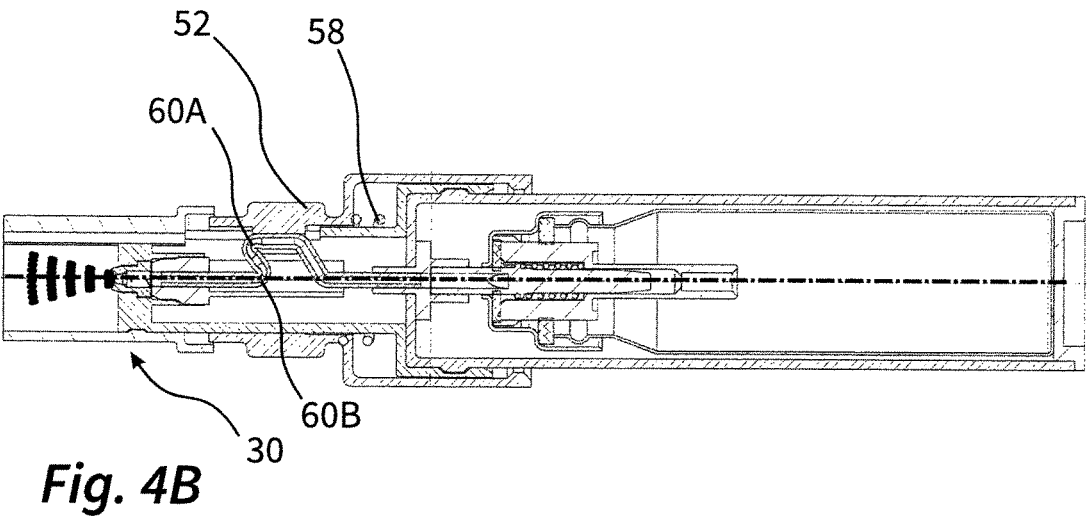

FIGS. 4A and 4B show a clearly different design of a liquid dispenser 10. In the case of this design, the liquid channel 40 between the liquid store 20 and the mouthpiece 30 and the discharge nozzle unit 32 provided there is likewise realized in part by way of a hose portion 60. This hose portion is not compressed directly by way of a hose forming segment 54, however. The hose forming segment 54 which engages around a part portion of the hose portion 60 here rather ensures a movement of the hose portion 60, by way of which two bending points 60A, 60B can be opened and closed. If the actuating surface 52 which is provided on a sleeve-shaped body is moved to the right in relation to FIGS. 4A and 4B, the bending radius at the bending points 60A and 60B decreases. The consequence is that liquid can flow through the liquid channel 40 to the discharge nozzle unit 32. If the actuating surface 52 is released, the restoring spring 58 presses the actuating surface and also the hose forming segment 54 back into its left-hand end position, in which the bending angle and the curvature radius are changed in the region of the bending points 60A, 60B in such a way that these bending points together prevent the throughflow of liquid through the liquid channel 40.

In the case of a liquid dispenser in accordance with FIGS. 4A and 4B, the actuation does not have to take place at the actuating surface 52. It can also be provided as an alternative that the mouthpiece 30, but not the discharge nozzle unit 32, is connected in the axial direction fixedly to the component of the actuating surface 52, with the result that pressing of the mouthpiece 30 in the direction of the liquid store 20 brings about opening of the outlet valve arrangement 50.

Figure 5A:
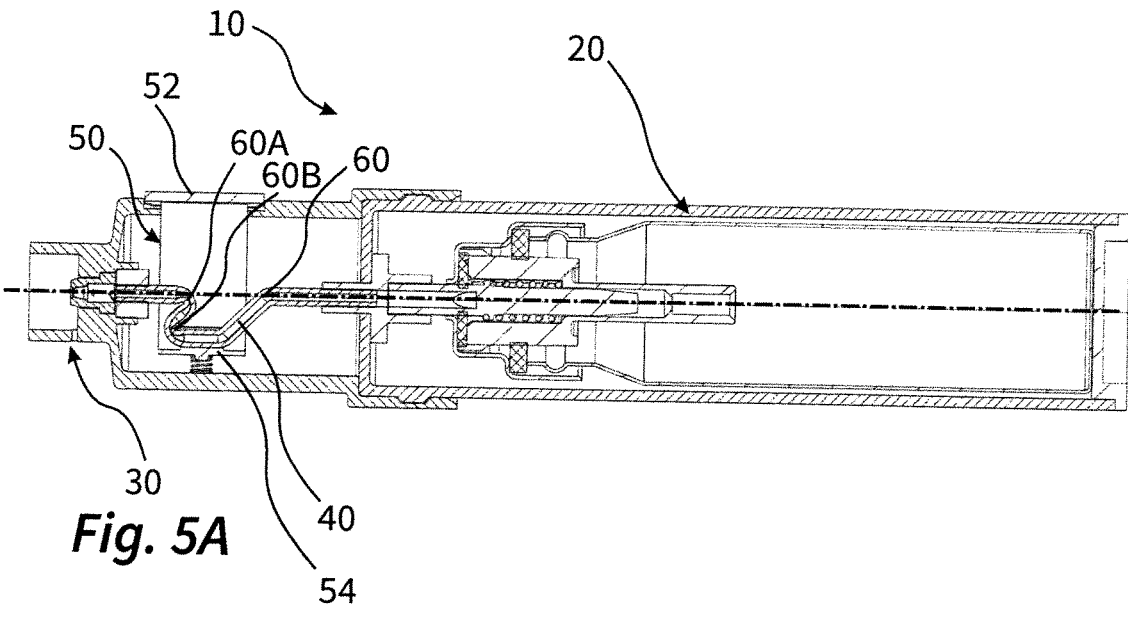
FIGS. 5A and 5B show the detailed construction of a fourth exemplary embodiment of a liquid dispenser according to the invention in the non-actuated state and in the actuated state.
Figure 5B:
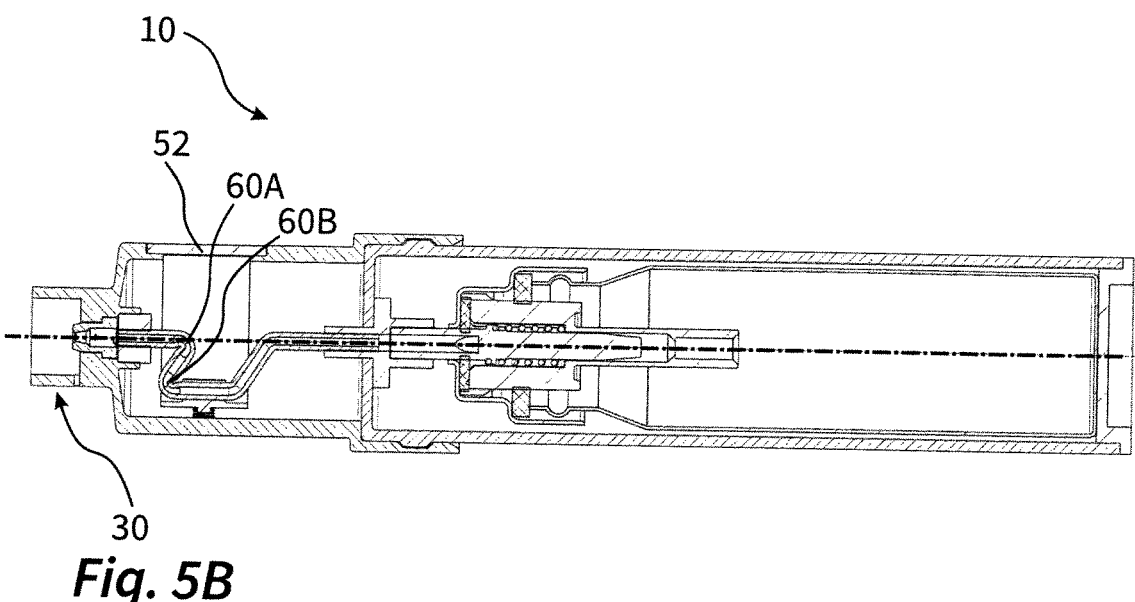

The design of FIGS. 5A and 5B is similar to that of FIGS. 4A and 4B, since a hose portion 60 is also used here which can bend in the region of two bending points 60A, 60B, in order to prevent a throughflow of liquid here from the liquid store 20 as far as the discharge nozzle unit 32. Unlike in the case of the design of FIGS. 4A and 4B, the corresponding deformation of the hose portion 60 for the purpose of opening and closing the outlet valve arrangement formed by it is not achieved by way of an axial movement, however, but rather by way of a radial movement. For this purpose, the actuating surface 52 can be pressed down, as a result of which the curvature radius and the curvature angle indirectly decrease in the region of the bending points 60A, 60B, with the result that liquid can then pass through the liquid channel 40 as far as the discharge nozzle unit 32.

Figure 6A:
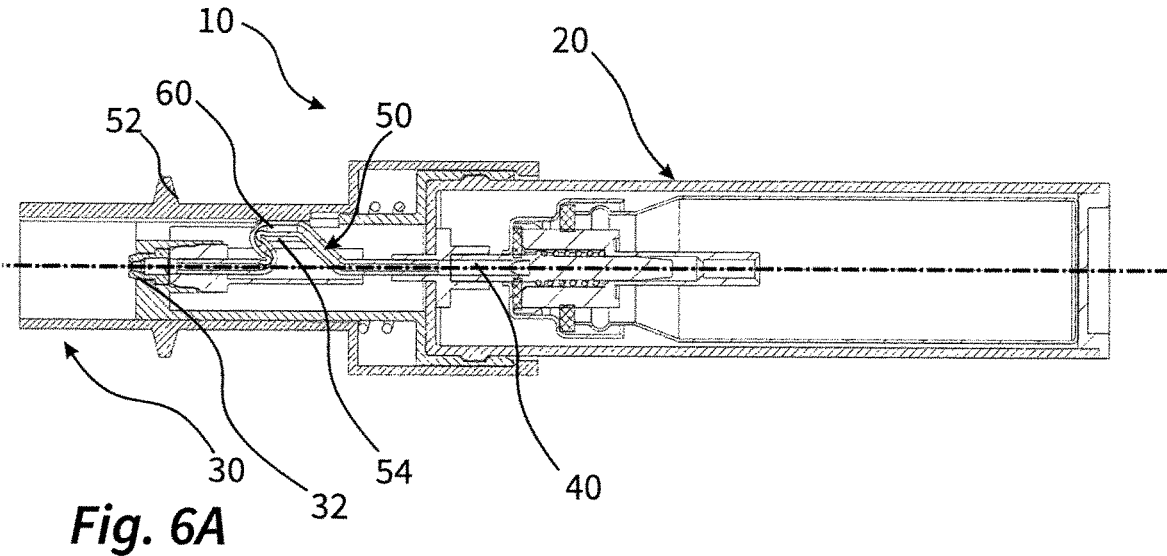
FIGS. 6A and 6B show the detailed construction of a fifth exemplary embodiment of a liquid dispenser according to the invention in the non-actuated state and in the actuated state.
Figure 6B:
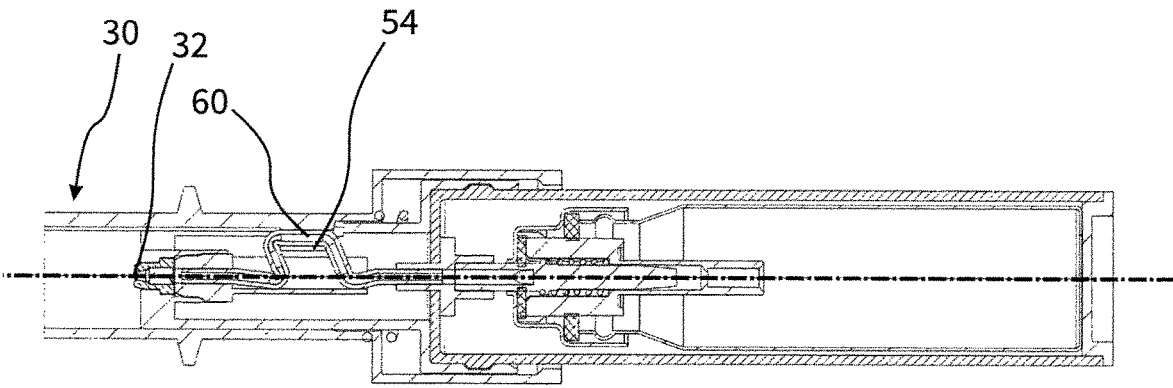

It is provided in the case of the design according to FIGS. 6A and 6B that a partial axial displacement of the hose portion 60 once again takes place. For this purpose, a single-piece component is provided which forms both the mouthpiece 30 and the hose forming segment 54. If, by way of the liquid store 20 being loaded with force, the hose portion is partially moved axially with respect to this component and the mouthpiece 30, relieving occurs at the bending points 60A, 60B, as a result of which liquid can pass as far as the discharge nozzle unit 32.

Figure 7A:
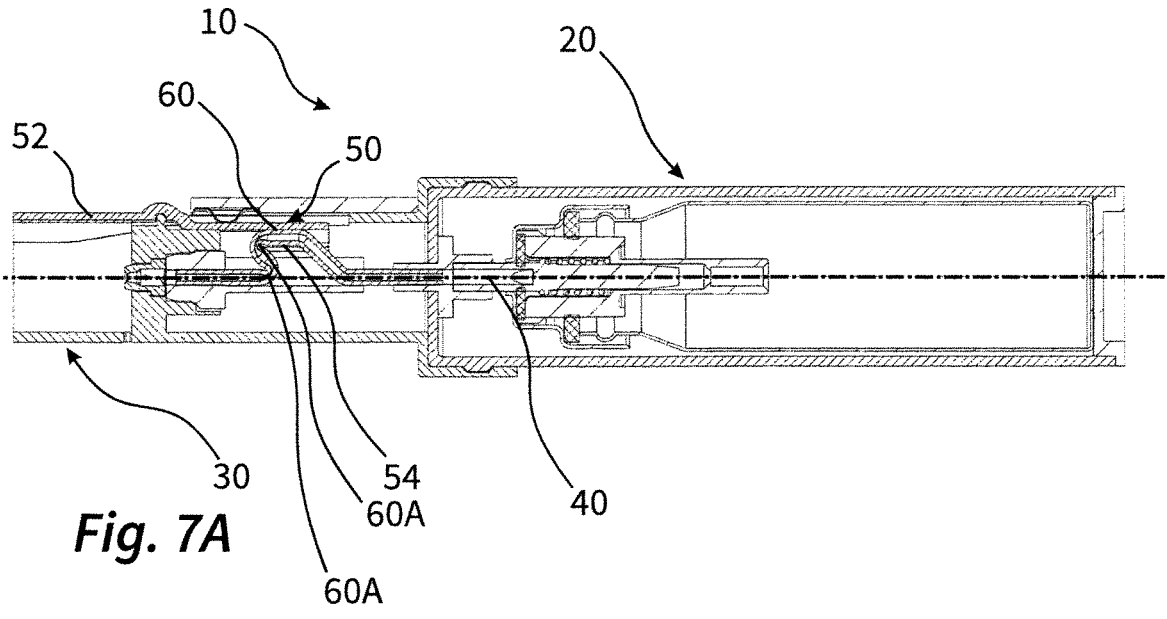
FIGS. 7A and 7B show the detailed construction of a sixth exemplary embodiment of a liquid dispenser according to the invention in the non-actuated state and in the actuated state.
Figure 7B:
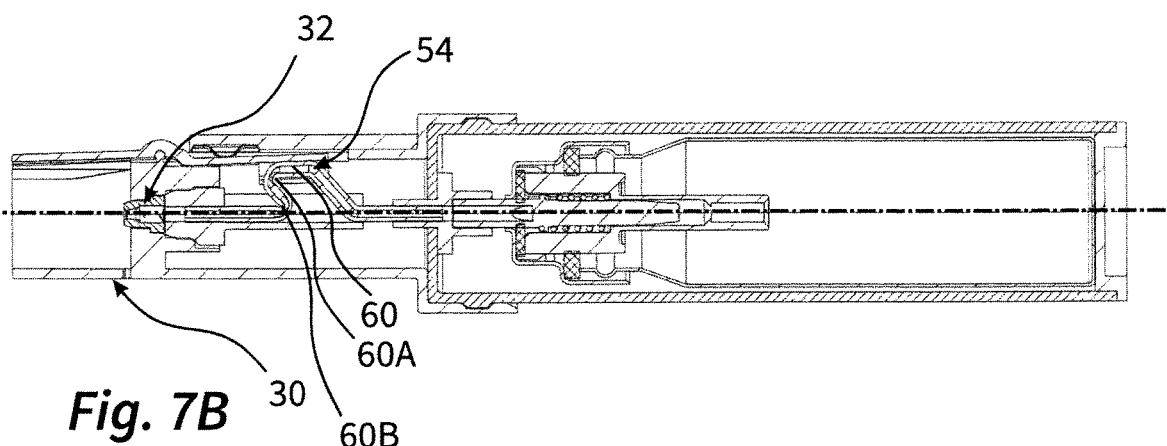

In a similar manner to the design of FIGS. 3A and 3B, a rocker-like element is provided in FIGS. 7A and 7B, on which rocker-like element both the actuating surface 52 which protrudes as far as the mouthpiece 30 and the hose forming segment 54 are provided. If the lips or the teeth are pressed together by the user, this rocker element pivots counter to the clockwise direction and counter to the force of the restoring spring 58. Here, the hose forming segment 54 is moved upward and therefore moves the hose portion 60 into the position of FIG. 7B, in which liquid can pass out of the liquid store 20 as far as the discharge nozzle unit 32.

FIG. 8 once again shows the shape, provided in the case of the designs of FIGS. 4A to 7B, of the hose portion 60 which describes approximately a parallelogram shape here. In addition to the two bending points 60A and 60B, there are also accordingly two curvature regions 60C and 60D. If the hose portion 60 is deformed for the purpose of opening the outlet valve arrangement, the curvature angle at the bending points 60A, 60B is reduced, while it is increased at the curvature points 60C and 60D in a way which is insignificant for the flow of liquid.

Figure 9:
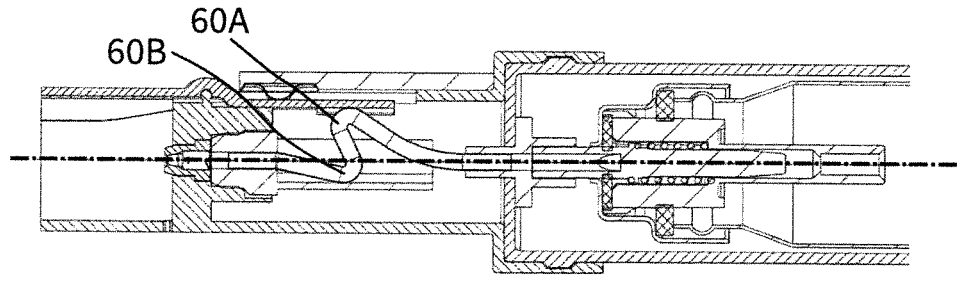

One alternative design can be gathered from FIG. 9. There are no curvature points 60C, 60D arranged in pairs here. Instead, the hose portion 60 is curved slightly in its entirety on both sides of the bending points at 60A, 60B, in order to achieve a situation where the two ends of the hose portion are in aligned orientation with respect to one another.

Figure 10:
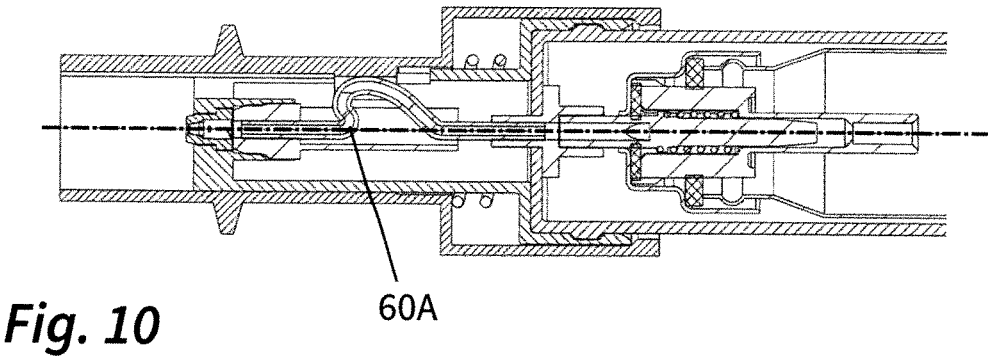

The design of FIG. 10 has only a single bending point 60A. Otherwise, the hose is routed as a result of a curvature which does not form a bending point in such a way that it forms said bending point 60A.

Figure 8:
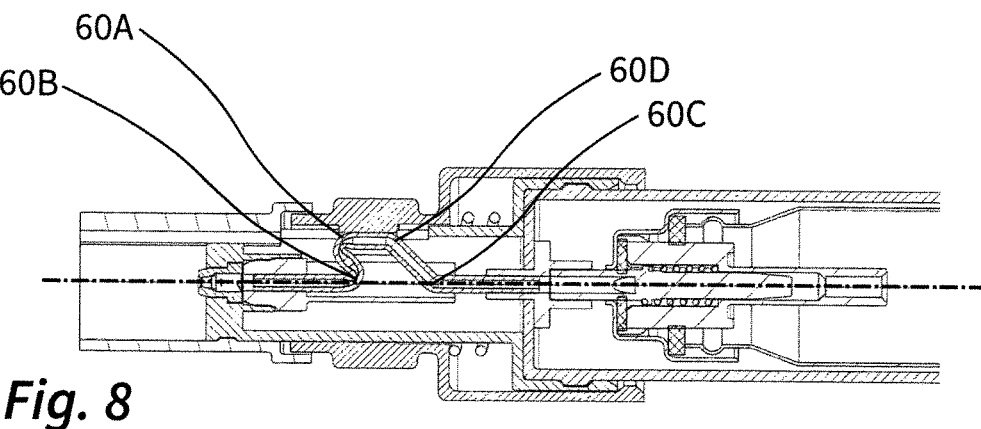
FIGS. 8 to 10 show alternative designs to the exemplary embodiments of FIGS. 6A to 7B.

All three hose designs of FIGS. 8 to 10 might be used in the case of the liquid dispensers of FIGS. 4A to 7B.

Figure 11A:
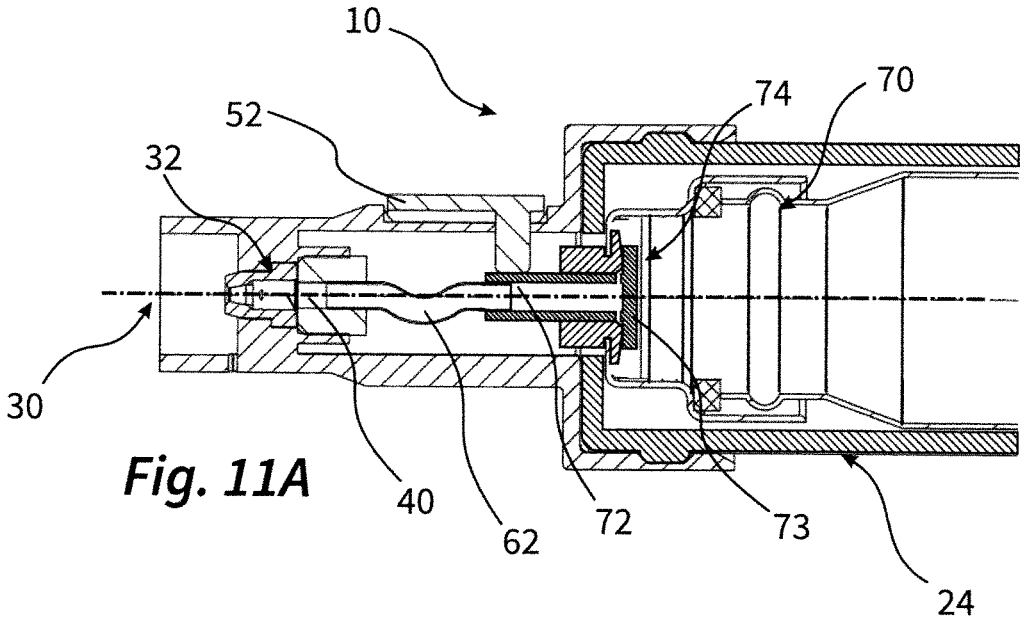
FIGS. 11A and 11B show the detailed construction of a further exemplary embodiment of a liquid dispenser according to the invention in the non-actuated state and in the actuated state.
Figure 11B:
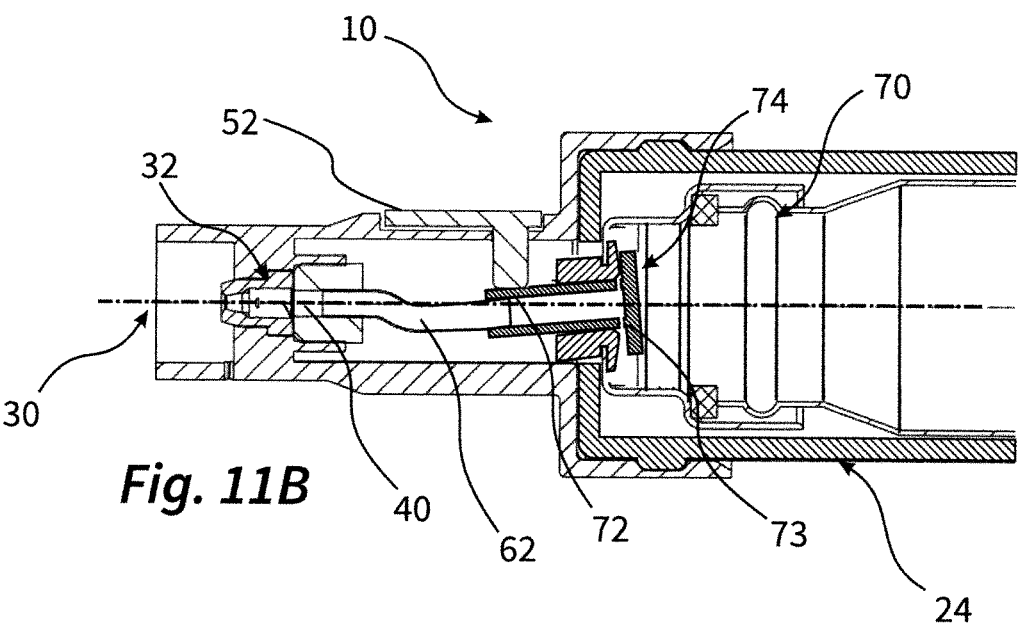

FIGS. 11A and 11B show a different design of an outlet valve arrangement. It is provided here that the outlet valve arrangement 70 which permits liquid to flow to the discharge nozzle unit 32 is designed in the manner of a tilt valve 74. In the case of the exemplary embodiments which are proposed here, this tilt valve 74 is connected fixedly to a liquid cartridge 24, but might also be configured separately from the liquid cartridge 24. The tilt valve 74 has an outlet nozzle 72 which merges at its right-hand end in the figures into a valve disk 73. If the outlet nozzle 72 is tilted, the valve surface 73 also tilts as a result and permits the discharge of liquid into the outlet nozzle 72 and from here through a hose portion 62 as far as the discharge nozzle unit 32.

It is provided in the case of the design of FIGS. 11A and 11B that a deflection of the outlet nozzle 72 takes place via an actuating surface 52 which is provided for manual actuation, as is illustrated in FIG. 11B. The hose portion 62 ensures here that the liquid which flows out through the outlet nozzle 72 is conducted to the discharge nozzle unit 32.

Figure 12:
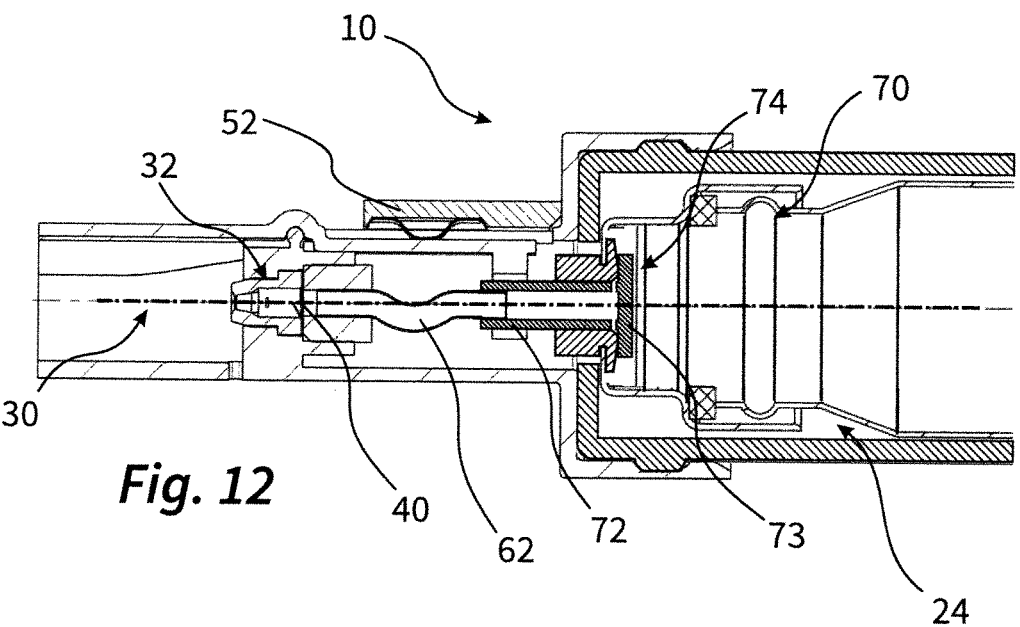
FIGS. 12 and 13 show alternative designs to the exemplary embodiments of FIGS. 11A and 11B.

A tilt valve 74 of the same type is likewise provided in the case of the variant of FIG. 12. This valve is opened in this case, however, by way of an actuation means which is moved by means of the mouth, that is to say by means of the teeth or the lips being pressed together. The actuating surface 52 is part of a rocker element, the end of which, which lies opposite the actuating surface 52, bringing about the tilting of the outlet nozzle 72 when the actuating surface 52 is pressed down.

Figure 13:
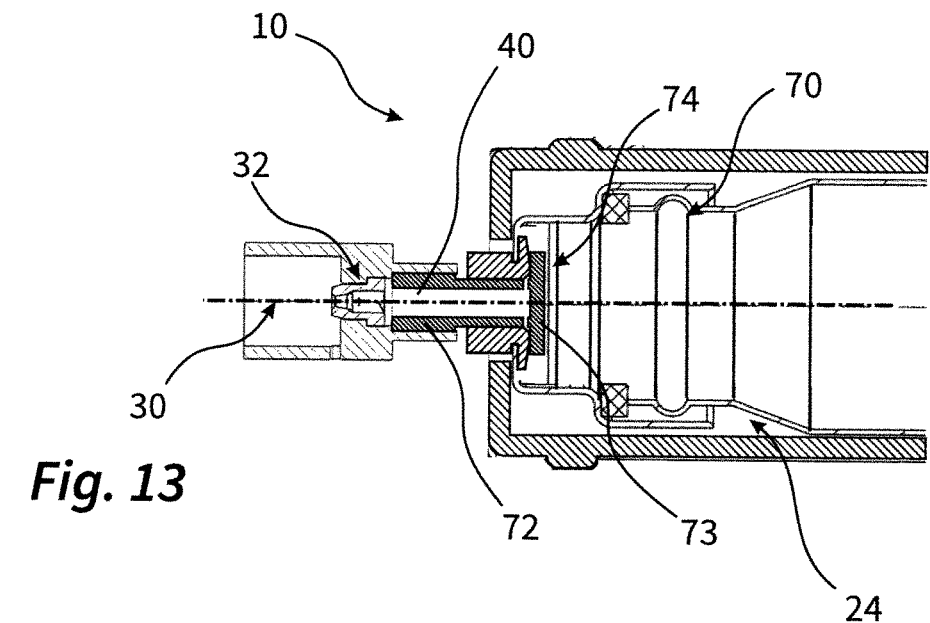

FIG. 13 shows a particularly simple design. A tilt valve 74 is also provided here. This valve is connected fixedly to the mouthpiece 30 in this case, however. Opening of the tilt valve takes place here by virtue of the fact that the user tilts the liquid store 20 slightly with respect to the mouthpiece 30. The liquid which flows out passes through the outlet nozzle 72 as far as the mouthpiece 30 and the discharge nozzle unit which is provided there.

The invention claimed is:

1. A dispenser for discharging a nicotine-containing and/ or cannabis-containing liquid, the dispenser comprising:
   a liquid store for storing liquid before discharge;
   a mouthpiece, through which mouthpiece the liquid is discharged;
   a liquid channel connecting the liquid store to the mouthpiece;
   a hose forming segment; and
   an outlet valve arrangement for closing and opening the liquid channel,
   the outlet valve arrangement having an elastically deformable hose portion forming a part of the liquid channel, and
   an actuating surface on an outer side of the dispenser, the actuating surface being movable with respect to the liquid store,
   the actuating surface being coupled to the hose forming segment, and when the actuating surface is loaded with force, the hose forming segment deforms the hose portion out of a state in which the hose portion closes the liquid channel and into a state in which the hose portion opens the liquid channel.

2. The dispenser as claimed in claim 1, wherein
   the hose forming segment is movable orthogonally with respect to the hose portion between
   a closing end position, the hose forming segment in the closing end position compressing the hose portion from outside the hose portion, and
   an opening end position, the hose forming segment in the opening end position moving away from the hose portion to therefore permit liquid flow through the hose portion.

3. The dispenser as claimed in claim 2, wherein
   the hose forming segment and the actuating surface are provided on sides of the hose portion lying opposite one another.

4. The dispenser as claimed in claim 1, wherein
   the hose forming segment is movable between
   a closing end position, the hose forming segment in the closing end position forcing the hose portion into a closed state, the hose portion in the closed state being bent at least once in at least one bending region such that inner surfaces of the hose portion lying opposite one another bear sealingly against one another to prevent flow of liquid through the hose portion, and
   an opening end position, the hose forming segment in the opening end position achieving a relieved state of the hose portion such that liquid can flow through the hose portion.

5. The dispenser as claimed in claim 4, further including a hose clamping-in region, and
   the hose portion has at least two bending regions between the hose forming segment and the hose clamping-in region.

6. The dispenser as claimed in claim 5, wherein
   in the at least two bending regions, the hose portion bends in opposite directions.

7. The dispenser as claimed in claim 5, wherein
   the at least two bending regions comprises a total of four bending regions forming corners of a parallelogram shape, two of the total of four bending regions being bent in a liquid-sealing manner upon arrangement of the hose forming segment in the closing end position.

8. The dispenser as claimed in claim 4, wherein
   the hose forming segment has a coupling portion, the hose portion in a region of the coupling portion bell fastened to the hose forming segment.

9. The dispenser as claimed in claim 1, wherein
   the actuating surface is configured for manual actuation.

10. The dispenser as claimed in claim 1, wherein
    no further valve at all for closing the hose portion is provided downstream of a point of the hose portion at which the hose portion is closed by the hose forming segment.

11. The dispenser as claimed in claim 1, wherein
    the actuating surface is configured for actuation by the mouth.

12. The dispenser as claimed in claim 11, wherein
    the actuating surface is disposed in a region of the mouthpiece and can be pressed down with the lips or teeth of the user, the actuating surface being attached in a pivotably movable manner to the mouthpiece.

13. The dispenser as claimed in claim 11, wherein
    the actuating surface is stationary with respect to the mouthpiece and is movable together with the mouthpiece axially in relation to a main direction of extent with respect to the liquid store.

14. The dispenser as claimed in claim 1, wherein
    the liquid store has a receptacle for receiving a liquid cartridge inserted into the receptacle.

15. The dispenser as claimed in claim 14, wherein
    the liquid store has an additional outlet valve openable via insertion of the liquid cartridge into the receptacle.

16. A dispenser for discharging a nicotine-containing and/or cannabis-containing liquid, the dispenser comprising:
    a liquid store for storing the liquid before discharge;
    a mouthpiece, through which mouthpiece the liquid is discharged;
    a liquid channel connecting the liquid store to the mouthpiece; and
    an outlet valve arrangement for closing and opening the liquid channel,
    the outlet valve arrangement having a tilt valve including a tiltably movable outlet nozzle penetrated by the liquid channel, the tilt valve being opened and closed based on a tilting position of the outlet nozzle.

17. The dispenser as claimed in claim 16, wherein
    the mouthpiece is configured for movement with respect to the liquid store and is coupled to the outlet nozzle of the outlet valve arrangement in such that a movement of the mouthpiece with respect to the liquid store pivots the outlet nozzle.

18. The dispenser as claimed in claim 17, wherein
    the mouthpiece is connected fixedly to the outlet nozzle.

19. The dispenser as claimed in claim 16, wherein
    the outlet valve arrangement has an actuating surface on an outer side of the dispenser, the actuating surface being movable with respect to the liquid store, and
    the actuating surface is operatively coupled to the outlet nozzle such that the outlet nozzle is pivotable by loading the actuating surface with force.

20. The dispenser as claimed in claim 16, further comprising
    a hose portion disposed between the outlet nozzle and the mouthpiece.

21. The dispenser as claimed in claim 16, wherein
the liquid store has a liquid cartridge with an outlet, the tilt valve being disposed at the outlet of the liquid cartridge.

22. The dispenser as claimed in claim 1, wherein
the dispenser has a discharge nozzle unit and liquid is discharged through the discharge nozzle unit into the mouthpiece.

23. The dispenser as claimed in claim 1, wherein
the dispenser has a restoring spring, the actuating surface being loaded with force in a direction of a non-actuated end position by the restoring spring.

24. The dispenser as claimed in claim 1, wherein:
the dispenser has an elongate shape extending in a direction of a main direction of extent; and/or
the liquid store of the dispenser extends in the direction of the direction of main extent; and/or
the mouthpiece of the dispenser extends in the direction of the direction of main extent.

25. The dispenser as claimed in claim 1, wherein:
the liquid store is filled with a nicotine-containing and/or cannabis-containing liquid; and/or
the liquid store is configured as a pressurized store for storing the liquid under pressure; and/or
the mouthpiece has a tubular design with an outlet opening, the outlet opening having an inside cross section of at least 20 mm$^2$; and/or
the mouthpiece has an air inlet channel configured as a radially oriented opening in a wall of the mouthpiece; and/or
the hose portion comprises an elastic material; and/or
at least a part of the hose portion has an internal diameter of 2.0 mm or less; and/or
at least a part of the hose portion has a wall thickness of less than 1.0 mm; and/or
at least a part of the hose portion has a wall thickness of at least 0.1 mm or more.

26. A dispenser for discharging a liquid, the dispenser comprising:
a liquid store configured as a pressurized store for storing the liquid before discharge;
a discharge opening, through which discharge opening liquid is discharged;
a liquid channel connecting the liquid store to the discharge opening;
an actuating surface; and
an outlet valve arrangement for closing and opening the liquid channel, the outlet valve arrangement having an elastically deformable hose portion forming a part of the liquid channel and
the outlet valve arrangement is configured as an outlet valve arrangement switchable by a user of the dispenser via the actuating surface between
an open state, wherein liquid flows through the hose portion in the open state, and
a closed state, the hose portion in the closed state being bent at least once in at least one bending region such that inner surfaces of the hose portion lying opposite one another bear sealingly against one another to prevent flow of liquid through the hose portion.

27. The dispenser as claimed in claim 26, wherein
no further valve at all for closing the hose portion is provided downstream of a point of the hose portion, at which the hose portion is closed by the hose forming segment.

28. The dispenser as claimed in claim 26, wherein the liquid store contains
a liquid medication or
a mouth spray or
a dental hygiene product.

29. The dispenser as claimed in claim 2, further including a tube portion partially enclosing the hose portion and having an inner circumference forming a holding surface, the hose portion bearing against the holding surface and being pressed against the holding surface by the hose forming segment in the closing end position.

30. The dispenser as claimed in claim 9, wherein:
the actuating surface is pressable in radially in relation to a main direction of extent to open the outlet valve arrangement; or
the actuating surface is movable axially in relation to the main direction of extent to open the outlet valve arrangement.

31. The dispenser as claimed in claim 21, wherein the liquid store has a receptacle for replaceably receiving the liquid cartridge.

32. The dispenser as claimed in claim 22, wherein:
the discharge nozzle unit has a plurality of nozzle openings; and/or
the discharge nozzle unit has a nozzle plate having a plurality of nozzle openings; and/or
the discharge nozzle unit includes at least 10 nozzle openings; and/or
the nozzle openings have an inside cross-section of no more than 250 μm$^2$ at a narrowest point.

* * * * *